(12) United States Patent
Janzen et al.

(10) Patent No.: US 11,345,883 B2
(45) Date of Patent: May 31, 2022

(54) BACTERIA

(71) Applicant: CHR. HANSEN A/S, Hoersholm (DK)

(72) Inventors: Thomas Janzen, Broenshoej (DK); Sonja Bloch, Copenhagen K (DK)

(73) Assignee: CHR. HANSEN A/S, Hoersholm (DK)

( * ) Notice: Subject to any disclaimer, the term of this patent is extended or adjusted under 35 U.S.C. 154(b) by 50 days.

(21) Appl. No.: 16/093,267

(22) PCT Filed: Apr. 12, 2017

(86) PCT No.: PCT/EP2017/058756
§ 371 (c)(1),
(2) Date: Oct. 12, 2018

(87) PCT Pub. No.: WO2017/178518
PCT Pub. Date: Oct. 19, 2017

(65) Prior Publication Data
US 2019/0382715 A1    Dec. 19, 2019

(30) Foreign Application Priority Data

Apr. 15, 2016 (EP) .................................. 16165621
May 11, 2016 (EP) .................................. 16169151

(51) Int. Cl.
| | |
|---|---|
| *C12N 1/20* | (2006.01) |
| *A23C 9/123* | (2006.01) |
| *C12N 9/10* | (2006.01) |
| *C12R 1/225* | (2006.01) |
| *C12R 1/245* | (2006.01) |

(52) U.S. Cl.
CPC .............. *C12N 1/20* (2013.01); *A23C 9/1234* (2013.01); *C12N 1/205* (2021.05); *C12N 9/1048* (2013.01); *A23Y 2220/17* (2013.01); *A23Y 2220/63* (2013.01); *C12R 2001/225* (2021.05); *C12R 2001/245* (2021.05)

(58) Field of Classification Search
CPC ........ C12N 1/20; C12N 1/205; C12N 9/1048; C12R 2001/225; C12R 2001/245; A23C 9/1234; A23C 19/0323; A23Y 2220/17; A23Y 2220/63; C07K 14/335
See application file for complete search history.

(56) References Cited

FOREIGN PATENT DOCUMENTS

| JP | S57-141293 A | 9/1982 |
|---|---|---|
| JP | S57-144939 A | 9/1982 |

OTHER PUBLICATIONS

Maze et al. Complete genome sequence of the probiotic Lactobacillus casei strain BL23. J. Bacteriol. (2010), 192(10): 2647-2648.*
Dong et al. A one-step PCR-based method for rapid and efficient site-directed fragment deletion, insertion and substitution mutagenesis. Journal of Virological Methods (2008), 149:85-90.*
Alvarez et al., "Stable expression of the Lactobacillus casei bacteriophage A2 repressor blocks phage propagation during milk fermentation," Journal of Applied Microbiology, vol. 86 (May 1999) pp. 812-816.
Capra et al., "Isolation and phenotypic characterization of Lactobacillus casei and Lactobacillus paracasei bacteriophage-resistant mutants," Journal of Applied Microbiology, vol. 111, (Aug. 2011) pp. 371-381.
Capra et al., "Technological and probiotic characterisation of Lactobacillus casei/paracasei strains and their phage-resistant mutants," International Dairy Journal, vol. 37, (Jul. 2014) pp. 39-47.
Ito et al., "Transposon Mutagenesis of Probiotic Lactobacillus casei Identifies asnH, an Asparagine Synthetase Gene Involved in Its Immune-Activating Capacity," Pios One, vol. 9, Issue 1, E83876 (Jan. 2014).
Martin et al., "Generation of Food-Grade Recombinant Lactic Acid Bacterium Strains by Site-Specific Recombination," Applied and Environmental Microbiology, (Jun. 2000) Vo. 66, No. 6, pp. 2599-2604.
Watanabe et al., "Cell surface characteristics of some phage-resistant strains of Lactobacillus casei", Journal of Applied Bacteriology, vol. 63, pp. 197-200 (1987).
Watanabe et al., "A Phage-resistant Mutant of Lactobacillus casei which Permits Phage Adsorption but Not Genome Injection," Journal of General Virology, vol. 65, (May 1984) pp. 981-986.

* cited by examiner

*Primary Examiner* — Iqbal H Chowdhury
(74) *Attorney, Agent, or Firm* — Foley & Lardner LLP

(57) ABSTRACT

The present invention relates to a novel *Lactobacillus* strain that is not attacked by common phages and a novel *Lactobacillus* strain with improved cell count stability, its use in the manufacture of fermented milk-based products, and novel milk based products containing the strain.

Figure 1:
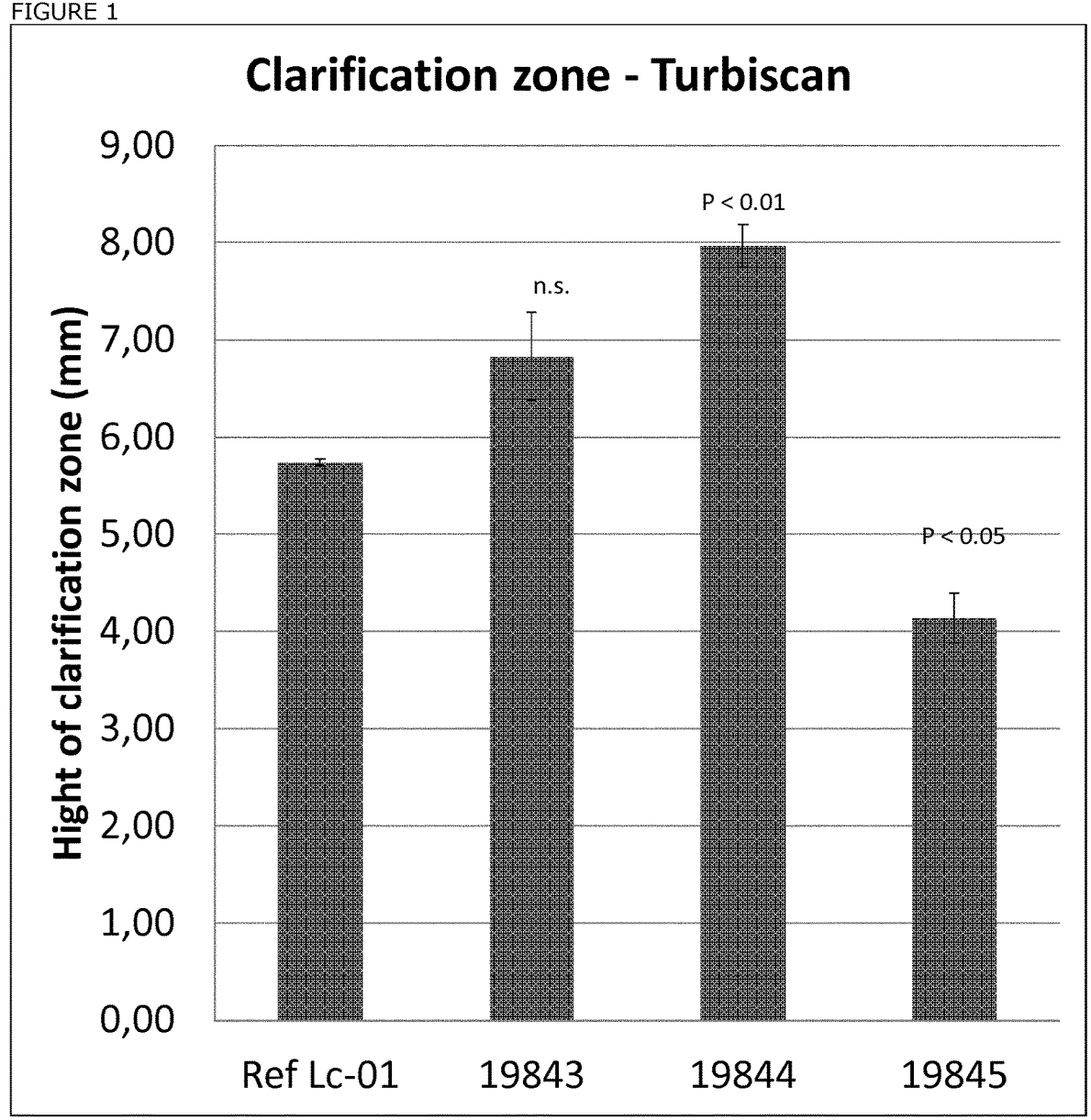

18 Claims, 3 Drawing Sheets
Specification includes a Sequence Listing.

BACTERIA

CROSS-REFERENCE TO RELATED APPLICATIONS

The present application is the U.S. National Stage of International Application PCT/EP2017/058756, filed Apr. 12, 2017, and claims priority to European Patent Application No. 16165621.0, filed Apr. 15, 2016 and European Patent Application No. 16169151.4, filed May 11, 2016.

FIELD OF INVENTION

The present invention relates to a novel *Lactobacillus* strain that is not attacked by common phages, its use in the manufacture of fermented milk-based products, and novel milk based products containing the strain. In a related aspect, the present invention relates to methods for improving the cell count stability of Lactobacilli such as *Lactobacillus paracasei*.

BACKGROUND OF INVENTION

Fermented milk products, such as fermented milk drinks, lactic acid bacteria beverages, yoghurt, cultured milks and cheese, are often produced by providing milk substrates, esp. based on animal milks, such as cow milk, goat milk, sheep milk and the like, as culture media and fermenting the medium with lactic acid bacteria. During the production of a fermented milk product, phages may attack the bacteria, leading to a reduction in the viable cell count of the lactic acid bacteria.

Especially fermented milk products which are consumed as health-promoting foods having physiological effects, such as intestinal function controlling effect and immunopotentiating effect, are dependent on a high number of viable bacteria. Production of fermented milk products comprising probiotic bacteria of the species *Lactobacillus paracasei* or *casei* is often challenged by phage attacks in the dairies, resulting in a product with lowered content of viable bacteria. For instance, the strain Lb. *paracasei* LC-01 (CHCC2115) was repeatedly attacked by bacteriophages in different dairies. It is however difficult to replace a strain susceptible to phage attack by another strain of the same species, as the replacement strain seldom has a similar functionality, such as acidification activity, flavor profile and/or the same probiotic character.

It has been suggested to obtain phage resistant strains, and methods for obtaining a phage resistant *Lactobacillus casei* strain are taught:

JP1341782C3 discloses the strain *Lactobacillus casei* YIT-9029 (FERM-P No. 5852) which is obtained by removing a prophage from the strain YIT-9018 (FERM-P No. 4751.

JP patent 19861005712 B4 discloses that a bacterial strain resistant to bacteriolysis is obtained by separating a temperature-sensitive mutant from *Lactobacillus casei* having prophage FSW (e.g. *Lactobacillus casei* YIT-9018) by mutagenic treatment, and removing the prophage FSW from the strain by thermal induction process.

However, these methods seem only to work with strains which contain a prophage.

Concurrently, the recent focus on the health related beneficial effects of live bacteria as well as extended shelf-life has led to higher demands for Lactic acid bacteria with extended viability such as improved cell count stability.

SUMMARY OF INVENTION

Thus, an objective of the present invention is to provide a method to obtain phage resistant mutants of strains of *Lactobacillus paracasei* or *casei* as well as mutants of strains of *Lactobacillus paracasei* or *casei* with increased cell count stability.

The present inventors have found that mutagenesis in combination with phage challenging and screening resulted in phage resistant strains which could replace the mother strain in fermented milk drinks.

Surprisingly, the inventors discovered that the mutant strains had improved properties compared to the mother strain, as it turned out that milk fermented with the strains of the invention had a significant lower degree of sedimentation, compared to fermented milk produced with the mother strain. This reduces the need for addition of stabilizer and/or thickeners to fermented milk products.

Further in a closely related aspect, the inventors have developed a method for improving the cell count stability of Lactobacilli and have found new strains exhibiting improved cell count stability.

More specifically the inventers found that by amending a gene coding for a glycosyltransferase, by truncation and a membrane protein involved in the export of O-antigen and teichoic acid (RfbX) it is possible to obtain a mutant with improved cell count stability.

More specifically, the mutant having improved cell count stability has a deletion of one nucleotide C (position 202 of the reference gene from CHCC2115), resulting in a truncated glycosyltransferase gene, and a mutation in a gene with homology to eps7M from *Lactobacillus casei* BL23 as also seen for CHCC19844. The gene product of eps7M is a part of a cell wall polysaccharide gene cluster. Gene comparison showed also homology to a "membrane protein involved in the export of O-antigen and teichoic acid (RfbX)".

The eps7M homolog is located three genes downstream from the glycosyltransferase.

Both mutations are in the same area. Based on the homology to genes involved in cps production it is evident that the identified mutations are responsible for the phage resistance phenotype.

The cell count stabilized strain CHCC19845 has a double mutation, in addition to a modified membrane protein, it also has a truncated glycosyltransferase, and both mutations are located in the same cell wall polysaccharide operon. It was surprisingly found that a double mutation event in this gene cluster is resulting in an extraordinary phage resistance as well as increased cell count stability.

Definitions

In the present context, the term "resistant to phage" refers to the lactic acid bacterium strain is able to propagate (at optimal growth temperature) in milk which contains 1000 phages per ml, i.e. the bacterium is able to reach a cell density above 10E8 cfu/ml after 48 hours when inoculated at a concentration of 10E5 cfu/ml. Cfu is "cell forming units".

The term "cell count stability" should be understood as a measure of the amount of colony forming units (CFU) per gram product. The higher *Lactobacillus* CFU/g over time, the more cell count stable is the tested strain. The cell count stability may be measured using the pour plate method.

The term "essentially inactive" should be understood in relation to the objective of the present invention, wherein the objective is to (essentially) inactivate a gene encoding a phage receptor protein, e.g. the eps7M gene.

The objective is to make a strain where the phage receptor protein works substantially worse than in a corresponding parent or wild-type strain. As explained below it is routine work for the skilled person to make such a strain. For instance by introducing a stop codon or a frame shift insertion in the phage receptor gene, which could give a non-functional gene that would e.g. either express no phage receptor protein or express a partial length inactive phage receptor protein. Alternatively, a mutation could be made in a promoter, or the gene, which e.g. could give a phage receptor protein mutation variant that has some activity but which for all herein related practical objectives is essentially inactive. A way to measure the inactivity of the phage receptor protein is simply to analyze the bacterium for increased resistance to a suitable representative panel of different bacteriophages. As explained below this is routine work for the skilled person and if the bacterium as described herein has a substantial increased resistance to the panel of bacteriophages then it is herein understood that the phage receptor protein is essentially inactive.

Inactivation of the phage receptor protein does generally not negatively affect viability, growth rate or acid production of the LAB. See working examples herein where this is demonstrated for two different strains.

Other genes involved in phage resistance can (essentially) be inactivated in line with the above methods.

By the expression a "phage receptor protein is functional inactive with respect to phage infection" is referred to a phage receptor protein which differs from the phage receptor protein sequence SEQ ID No. 2 and which is characterized by that a bacterium which carries a phage receptor gene coding for said functional inactive phage receptor protein has improved resistance to at least one bacteriophage, especially the bacteriophage CHPC1256.

The term "improved resistance to a bacteriophage" denotes that the bacteria strain when tested in a plaque assay, such as the assay "determination of phage resistance by the agar overlay method" described below have an improved phage resistance to at least one phage expressed as the difference in pfu/ml (plaque forming unit per ml) obtainable with said at least one bacteriophage on the given strain, compared to the pfu/ml obtainable with the same bacteriophage on the parent strain. A strain with improved resistance to a bacteriophage preferably show a reduction of pfu/ml of a factor at least 50, such as at least 100, e.g. 500, preferably at least 1000, more preferably at least a factor 10000 or more.

Methods to Essentially Inactivate the Phage Receptor Protein

As discussed above, it is routine work for the skilled person to make a strain as described herein, where the phage receptor protein is essentially inactive.

Generally speaking a suitable routine method may be to introduce or replace via homologous recombination a suitable DNA fragment into the phage receptor genomic gene sequence (e.g. by use of the publicly available pGhost vectors). If the introduced fragment for instance comprises a nonsense (stop) codon then the gene would be inactivated and the LAB will be a LAB with an inactive phage receptor protein. Another suitable modification could be a frameshift mutation, a deletion, a mutation or an insertion. Alternatively, a suitable modification may be introduced into a related region such as the promoter region.

As explained above a suitable modification of the phage receptor gene may be many things such as a stop codon, an insertion that e.g. cause frame shift, a deletion, a promoter mutation, a mutation, etc.

It is routine work for the skilled person to choose an adequate strategy to e.g. introduce a suitable modification of the phage receptor gene in order not to get expression of an active phage receptor protein.

Alternatively, one may randomly mutagenize (e.g. by UV radiation or chemical mutagenesis) and select for mutations wherein the phage receptor protein is essentially inactive. Further one could select for relevant spontaneous mutations, wherein the phage receptor protein is essentially inactive.

In a preferred embodiment the phage receptor protein is inactive.

Methods to Assay Protein Inactivation

As said above, a way to measure the inactivity of the phage receptor protein is simply to analyze the bacterium for increased resistance to bacteriophages.

Routinely this may be done by use of a standard plaque assay. The plaque assay evaluates the phage resistance of a strain of interest as the difference in pfu/ml (plaque forming units per ml) obtainable with a given bacteriophage on the strain of interest, compared to the pfu/ml obtainable with the same bacteriophage on the parent strain.

Accordingly, a lactic acid bacterium as described herein may be characterized by that it has improved resistance to the bacteriophage and/or improved cell count stability.

Preferably, the lactic acid bacterium as described herein has improved resistance to the phage deposited according to the present invention.

An alternative way to measure the inactivity of the protein is to analyze the corresponding gene sequence to see if it comprises a suitable modification that cause e.g. an inactivation of the gene. As explained above a suitable modification may be many things such as a stop codon, an insertion that e.g. cause frame shift, a deletion, a mutation etc. It is routine for a skilled person (e.g. by sequencing the gene) to identify if the gene comprises such a suitable modification.

Accordingly, in a preferred embodiment the lactic acid bacterium as described herein comprises a suitable modification in the gene, wherein the modification results in that essentially no active protein is expressed. More preferably, the modification results in that no active protein is expressed.

A further way to measure the inactivity of the protein is to analyze if active protein is present in the membrane of the bacterium. This may be done by a standard isolation method as described in working examples herein.

Accordingly, in a preferred embodiment the lactic acid bacterium as described herein does not comprise measurable amount of active protein in the membrane.

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes the two interesting species of the present invention: *Lactobacillus paracasei* and *Lactobacillus casei*. Examples on species are: *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Lactic acid bacteria, including bacteria of the species *Lactobacillus*, are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product. Such cultures are in general referred to as "starter cultures" or "starters".

In the present context, the term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder. Preferably, at least part of the protein in the milk substrate is proteins naturally occurring in milk, such as casein or whey protein. However, part of the protein may be proteins which are not naturally occurring in milk. Prior to fermentation, the milk substrate may be homogenized and pasteurized according to methods known in the art.

The term "milk" is to be understood as the lacteal secretion obtained by milking any mammal, such as cows, sheep, goats, buffaloes or camels. In a preferred embodiment, the milk is cow's milk. The term milk also comprises milks derived from plant material, such as soy milk. Optionally the milk is acidified, e.g. by addition of an acid (such as citric, acetic or lactic acid), or mixed, e.g. with water. The milk may be raw or processed, e.g. by filtering, sterilizing, pasteurizing, homogenizing etc, or it may be reconstituted dried milk. An important example of "bovine milk" according to the present invention is pasteurized cow's milk. It is understood that the milk may be acidified, mixed or processed before, during and/or after the inoculation with bacteria.

The term "fermented milk drink" is a drinkable product obtained by fermentation of a milk substrate with lactic acid bacteria, such as bacteria of the species *Lactobacillus paracasei*. The product may be drinkable from a cup or a bottle, or via a straw. The product may be homogenized, e.g. after fermentation.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Fermentation" in the methods of the present invention means the conversion of carbohydrates into alcohols or acids through the action of a microorganism. Preferably, fermentation in the methods of the invention comprises conversion of lactose to lactic acid. Fermentation processes to be used in production of fermented milk products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a fermented milk product.

In the present context, the term "packaging" (a suitable amount of) the fermented milk in a suitable package relates to the final packaging of the fermented milk to obtain a product that can be ingested by e.g. a person or a group of persons. A suitable package may thus be a bottle or similar, and a suitable amount may be e.g. 10 ml to 5000 ml, but it is presently preferred that the amount in a package is from 50 ml to 1000 ml.

In the present context, the term "mutant" should be understood as a strain derived from another strain (mother strain) by means of e.g. mutagenesis, radiation and/or chemical treatment, and/or selection, adaptation, screening, etc. The term also includes mutants with improved or altered phage resistance, e.g. phage hardened mutants or mutants showing improved cell count stability. It is preferred that the mutant is a functionally equivalent mutant, e.g. a mutant that has substantially the same, or improved, properties (e.g. regarding yield, viscosity, gel stiffness, mouth coating, flavor, post acidification, acidification speed, and/or phage robustness) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenization step followed by a screening/selection step), but it is presently preferred that no more than 1000, no more than 100, no more than 20, no more than 10, or no more than 5, treatments are carried out. In a presently preferred mutant, less than 5%, or less than 1% or even less than 0.1% of the nucleotides in the bacterial genome have been changed (such as by replacement, insertion, deletion or a combination thereof) compared to the mother strain.

In the present context, the term "variant" should be understood as a strain which is functionally equivalent to a strain of the invention, e.g. having substantially the same, or improved, properties e.g. regarding viscosity, gel stiffness, mouth coating, flavor, post acidification, acidification speed, sedimentation, probiotic activity, and/or phage robustness). Such variants, which may be identified using appropriate screening techniques, are a part of the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

In further aspects, the present invention may be summarized by the following items:

Item 1. A strain of the species *Lactobacillus paracasei* or *Lactobacillus casei*, said strain is resistant against infection with the phage CHPC1256, deposited as DSM32286 or mutants or variants of this phage.

Item 2. A strain of the species *Lactobacillus paracasei* or *Lactobacillus casei*, wherein said strain maintain a viability (CFU/g) of at least 75%, such as e.g. 80%, 85%, 90% or 95% after 40 days of storage at 5 degree celsius in a fermented milk matrix.

Item 3. A strain according to item 2, wherein the strain is inoculated in a rate of around 10^9 CFU per kg milk, and optionally as single acidifier.

Item 4. A strain according to any of items 1 to 3 wherein said strain has a mutation in the gene eps7M, said mutation results in a change in the structure of the encoded protein and/or said strain has a mutation (e.g resulting in truncation) in the gene LCABL_02330 coding for a glycosyltransferase, said mutation results in partly or fully inactivation of the enzyme having glycosyltransferase activity.

Item 5. A strain of the species *Lactobacillus paracasei*, said strain is resistant against infection with the phage CHPC1256 (DSM32286) or mutants or variants of this phage.

Item 6. The strain of the preceding item, which has been obtained by exposing a non-phage resistant strain of the species *Lactobacillus paracasei* or *Lactobacillus casei* to a phage, and selecting a phage resistant mutant strain.

Item 7. The strain of any preceding item, which has been obtained by
subjecting a non-phage resistant strain of the species *Lactobacillus paracasei* or *Lactobacillus casei* for mutagenesis;
exposing the mutated strains of the species *Lactobacillus paracasei* or *Lactobacillus casei* to a phage;
selecting a phage resistant mutant strain.

Item 8. The strain of preceding items 4-7, wherein the phage is CHCP1256 or mutants or variants of this phage.

Item 9. The strain of any preceding item 4-8, wherein the non-phage-resistant strain of the species *Lactobacillus paracasei* or *Lactobacillus casei* is selected from the group comprising LC-01 (DSM19465), *L. casei* DG (CNCM I-1572), LPC-37 (ATCC SD5275), CHCC14676 (DSM25612) *L. casei* 431 (CRL431), ATCC 55544, *Lactobacillus paracasei* F19, LMG-17806, *Lactobacillus paracasei* subsp. *paracasei* LP-33, CCTCC M204012, and CNCM I-1518, or mutants or variants of any of these.

Item 10. The strain of any preceding items 6-9, wherein the phage-sensible strain of the species *Lactobacillus paracasei* is LC-01 (DSM19465), or a mutant thereof.

Item 11. A strain which is obtainable by a method comprising the following steps:
subjecting the *Lactobacillus paracasei* strain LC-01 (DSM19465) to mutagenesis;
exposing the mutated strains to the phage CHPC1256 (DSM32286);
selecting a strain which is resistant against the phage CHCP1256.

Item 12. The strain *Lactobacillus paracasei* CHCC19845, deposited as DSM 32276, and mutants or variants of this strain.

Item 13. The strain *Lactobacillus paracasei* CHCC19845, deposited as DSM 32276, and mutants thereof which have the same (or substantially the same) or improved functionality, such as with respect to phage resistance or sedimention or cell count stability.

Item 14. The strain *Lactobacillus paracasei* CHCC19845.

Item 15. The strain *Lactobacillus paracasei* CHCC19843, and mutants or variants of this strain.

Item 16. The strain *Lactobacillus paracasei* CHCC19844, and mutants or variants of this strain Item 17. The strain *Lactobacillus paracasei* CHCC2115 (DSM19465), and mutants or variants of this strain.

Item 18. The phage CHPC1256 (DSM32286), and mutants or variants of this phage.

Item 19. A strain of the species *Lactobacillus paracasei* or *Lactobacillus casei*, said strain has a mutation in the gene eps7M, said mutation results in a change in the structure of the encoded protein.

Item 20. A strain of the species *Lactobacillus paracasei* or *Lactobacillus casei*, wherein the protein encoded by the gene eps7M is essential inactive, with respect to phage infection.

Item 21. A strain of the species *Lactobacillus paracasei* or *Lactobacillus casei*, wherein the protein encoded by the gene eps7M is essential inactive, with respect to infected with the phage CHPC1256, deposited as DSM32286, or mutants or variants of this phage Item 22. The strain according to the preceding item, wherein the protein is expressed by a gene comprising a DNA sequence selected from the group consisting of:
(a) the DNA sequence shown in SEQ ID NO 1; and
(b) a DNA sequence that encodes a polypeptide, that is at least 70% identical to the polypeptide sequence shown in SEQ ID NO 2.

Item 23. The strain of the preceding item, wherein said essentially inactive protein is functional inactive with respect to phage infection, e.g. with the phage CHCP1256.

Item 24. A strain of the species *Lactobacillus paracasei* or *Lactobacillus casei*, said strain has a mutation (e.g resulting in truncation) in the gene LCABL_02330 coding for a glycosyltransferase, said mutation results in partly or fully inactivation of the enzyme.

Item 25. A strain of the species *Lactobacillus paracasei* or *Lactobacillus casei*, wherein the protein encoded by the gene LCABL_02330 (coding for a glycosyltransferase), is essential inactive, e.g. enzymatically inactive.

Item 26. The strain according to the preceding item, wherein the protein is expressed by a gene comprising a DNA sequence selected from the group consisting of:
(a) the DNA sequence shown in SEQ ID NO 3; and
(b) a DNA sequence that encodes a polypeptide, that is at least 70% identical to the polypeptide sequence shown in SEQ ID NO 4.

Item 27. The strain of the preceding item, wherein said essentially inactive protein is functional inactive with respect to phage infection, e.g. with the phage CHCP1256.

Item 28. A strain of the species *Lactobacillus paracasei* or *Lactobacillus casei*, said strain has a mutation in the gene LCABL_02330 coding for a glycosyltransferase, and a mutation in the gene eps7M.

Item 29. A strain of the species *Lactobacillus paracasei* or *Lactobacillus casei*, wherein the protein encoded by the gene LCABL_02330 (coding for a glycosyltransferase), and the protein encoded by the gene eps7M, both are essential inactive.

Item 30. The strain of the preceding item, wherein said essentially inactive proteins are functionally inactive with respect to phage infection, e.g. with the phage CHCP1256.

Item 31. The strain of any of the preceding items, wherein the protein is inactive due to that a suitable modification (mutation) has been introduced into the gene preferably a suitable modification selected from the group consisting of a stop codon, an insertion that e.g. cause frame shift, a deletion, and a mutation.

Item 32. The strain of any preceding item, wherein the strain is of the species *Lactobacillus paracasei*.

Item 33. The strain of the preceding items, which is the strain *Lactobacillus paracasei* CHCC19845, deposited as DSM 32276, or a mutant thereof.

Item 34. The strain of any preceding item, wherein bacteria of said strain have an improved resistance to a bacteriophage, e.g. preferably show a reduction of plague forming units (pfu)/ml of a factor at least 50, such as at least 100, e.g. 500, preferably at least 1000, more preferably at least a factor 10000 or more.

Item 35. A method for manufacture of a phage resistant mutant of a strain of the species *Lactobacillus paracasei* or *Lactobacillus casei*, said method comprises:
subjecting a culture of the strain (the mother strain) for mutagenesis;
exposing the mutated strains for a phage that attacks the mother strain
selecting a phage resistant mutant.

Item 36. A method for manufacture of a cell count stabilized mutant of a strain of the species *Lactobacillus paracasei* or *Lactobacillus casei*, said method comprises:
subjecting a culture of the strain (the mother strain) for mutagenesis;
exposing the mutated strains for a phage that attacks the mother strain
selecting a cell count stabilized mutant.

Item 37. A method for manufacture of a mutant, which has a lower sedimentation rate than the mother strain, of a strain of the species *Lactobacillus paracasei* or *Lactobacillus casei*, said method comprises the following steps:
subjecting a culture of the strain (the mother strain) for mutagenesis;
exposing the mutated strains for a phage that attacks the mother strain
selecting a phage resistant mutant.

Item 38. The method according to any preceding item, wherein the mother strain is selected from the group consisting of CHCC2115 (DSM19465), LC-01 (DSM19465), *L. casei* DG (CNCM I-1572), LPC-37 (ATCC SD5275), CHCC14676 (DSM25612), *L. casei* 431 (CRL431), ATCC 55544, *Lactobacillus paracasei* F19, LMG-17806, *Lactobacillus paracasei* subsp. *paracasei* LP-33, CCTCC M204012, and CNCM I-1518, or mutants or variants of any of these.

Item 39. The method according to any preceding item, wherein the phage is selected from the group consisting of CHPC1265, and mutants or variants of this phage.

Item 40. A method for providing a phage resistant mutant of Lb *paracasei* strain LC-01 (DSM19465), said method comprises:
subjecting a culture of the strain LC-01 for mutagenesis;
exposing the mutated strains for a phage that attacks the LC-01 strain; and
selecting a phage resistant mutant.

Item 41. A method for providing a mutant of Lb *paracasei* strain LC-01 (DSM19465), which mutant has a lower sedimentation rate than LC-01, said method comprises:
subjecting a culture of the strain LC-01 for mutagenesis;
exposing the mutated strains for a phage that attacks the LC-01 strain; and
selecting a phage resistant mutant, and
selecting a mutant with lower sedimentation rate.

Item 42. A method for providing a phage resistant mutant of a strain of the species *Lactobacillus paracasei* or *Lactobacillus casei*, said method comprises:
subjecting a culture of the strain (the mother strain) for mutagenesis;
exposing the mutated strains for the phage CHPC1256;
selecting a phage resistant mutant.

Item 43. A method for providing a phage resistant mutant of Lb *paracasei* strain LC-01 (DSM19465), said method comprises:
subjecting a culture of the strain LC-01 for mutagenesis;
exposing the mutated strains for the phage CHPC1256;
selecting a phage resistant mutant.

Item 44. A method for providing a phage resistant mutant of a strain of the species *Lactobacillus paracasei* (and/or *Lactobacillus casei*), said method comprises:
introducing a mutation (e.g. by means of genetic engineering) in the gene eps7M, said mutation results in a change in protein or in the CPS structure.

Item 45. A method for providing a phage resistant mutant of a strain of the species *Lactobacillus paracasei* (and/or *Lactobacillus casei*), said method comprises:
introducing a mutation (e.g. by means of genetic engineering) in the gene LCABL_02330 coding for a glycosyltransferase, said mutation results in a change in the CPS structure.

Item 46. The method of any preceding item, wherein the strain is of the species *Lactobacillus paracasei*.

Item 47. A strain of the species *Lactobacillus paracasei* or *Lactobacillus casei*, which is obtainable by a method of any preceding items.

Item 48. A strain of the species *Lactobacillus paracasei* or *Lactobacillus casei*, which is obtained by a method of any preceding items.

Item 49. Use of a strain of any preceding item for fermenting a milk substrate.

Item 50. Use of a strain of any preceding item as an additive, such as a probiotic additive.

Item 51. A bacterial culture, such as a starter culture, which contains at least 10E8 CFU per gram of a strain of any preceding item.

Item 52. The bacterial culture of the preceding item, which further contains an additive which acts as a stabilizer, such as a cryoprotectant.

Item 53. The bacterial culture of any preceding item, which is in frozen or dried form, such as freeze dried or spray dried.

Item 54. A food product containing a strain of any preceding items, such as a milk product or a cheese.

Item 55. A food product containing a strain of any preceding items, which is a cheese.

Item 56. A food product containing a strain of any preceding items, which is a fermented milk product, such as a drinking yogurt.

Item 57. The food product of any preceding item, which contain more than 10E8 colony forming units of lactic acid bacteria.

Item 58. The food product of any preceding item, which is packaged, e.g. in a container having a volume in the range of 50 ml to 1000 ml.

EXAMPLES

Example 1: Manufacture of Phage Resistant Mutants by Mutagenesis

Three phage resistant mutants from *Lactobacillus paracasei* LC-01 (CHCC2115), called CHCC19843, CHCC19844, and CHCC19845, were isolated by challenging a culture of LC-01 with the phage CHPC1256.

CHCC2115 was infected with phage CHPC1256 in MRS broth with 10 mM $CaCl_2$ at an MOI (multiplicity of infection) of 1, 0.1, or 0.01, and incubated 2 to 5 days until growth occurs in the tube. The cultures were streaked on MRS plates, colonies purified, and retested with phage CHPC1256 for phage resistance by plaque assay.

Example 2: Testing of Phage Resistant Mutant

Putative phage resistant mutants were tested in plaque assay on MRS plates with 10 mM $CaCl_2$.

CHCC19843 and CHCC19844 were resistant to CHPC1256, whereas CHCC19845 was resistant to all phages tested so far able to attack the mother strain LC-01.

TABLE 1

Results from plaque assay with phages attacking CHCC2115.
Phage titer is indicated in plaque forming units/ml.

|  | CHPC1054 | CHPC1135 | CHPC1167 | CHPC1259 | CHPC1256 |
| --- | --- | --- | --- | --- | --- |
| CHCC2115 | 3×e08 | 2×e09 | 5×e08 | 2×e10 | 9×e09 |
| CHCC19843 | 4×e07 | 1×e08 | 1×e08 | 2×e09 | Negative |
| CHCC19844 | 9×e08 | 3×e08 | 2×e08 | 2×e09 | Negative |
| CHCC19845 | Negative | Negative | Negative | Negative | Negative |

The mutant strain CHCC19845 was selected as the most promising strain as it surprisingly was found that this strain was extremely resistant against phage attack.

Example 3: Sequencing and Genome Analysis of the Promising Phage Resistant Mutants CHCC19844, and CHCC19845

The mutants CHCC19844 and CHCC19845 were fully genome sequenced and the genome sequences were compared with the one from CHCC2115.

Gene annotations were made with the RAST program (Rast Annotation using Subsystem Technology, vers. 2). Analysis for mutations was made with the CLC program (CLC Bio Qiagen).

CHCC19844:

Genome analysis of the mutant showed a mutation in a gene with homology to eps7M from *Lactobacillus casei* BL23 (locus tag "LCABL_RS01180", old locus tag "LCABL_02360", NCBI Reference Sequence of BL23: NC_010999.1).

The gene product of eps7M is a part of a cell wall polysaccharide gene cluster. Gene comparison showed also homology to a "membrane protein involved in the export of O-antigen and teichoic acid (RfbX)".

The mutation is a C to T nucleotide exchange at position 101 leading to a shift from amino acid proline to leucine. Based on the homology to genes involved in cps production it is evident that the identified mutation is responsible for the phage resistance phenotype.

CHCC19845:

Genome analysis of the mutant showed a mutation in gene LCABL_02330 coding for a glycosyltransferase.

The gene has a deletion of one nucleotide C (position 202 of the reference gene from CHCC2115), and is therefore resulting in a truncated glycosyltransferase gene.

In addition there was also a mutation in a gene with homology to eps7M from *Lactobacillus casei* BL23 as also seen for CHCC19844.

The mutation is a T to C nucleotide exchange at position 124 leading to a shift from amino acid phenylalanine to leucine. With this the eps7M mutations are different in CHCC19844 and CHCC19845.

The gene product of eps7M is a part of a cell wall polysaccharide gene cluster. Gene comparison showed also homology to a "membrane protein involved in the export of O-antigen and teichoic acid (RfbX)".

The eps7M homolog is located three genes downstream from the glycosyltransferase.

Both mutations are in the same area as the mutation found for CHCC19844.

Based on the homology to genes involved in cps production it is evident that the identified mutations are responsible for the phage resistance phenotype.

With this it was shown that capsular polysaccharides (cps) of the CHCC2115 cell wall are serving as phage receptor for all Lb. *paracasei* phages tested, and that inactivation or modification of cps related genes are leading to phage resistance, in the case of CHCC19845 an extremely strong resistance, since all phages tested so far are restricted.

CHCC19845 has a double mutation, in addition to a modified membrane protein, it also has a truncated glycosyltransferase, and both mutations are located in the same cell wall polysaccharide operon. It was surprisingly found that a double mutation event in this gene cluster is resulting in an extraordinary phage resistance.

Example 4: Manufacture of Milk Products Containing Phage Resistant Mutant—Assessment of Sedimentation Fermented diluted milk drinks were produced with the strains CHCC19843, CHCC19844, and CHCC19845, respectively, as single acidifier. Reconstituted skimmed milk (14%) with addition of 4% glucose (90° C., 60 minutes) was inoculated with a strain as single acidifier and fermented for approximately 72 hours. Thereafter, one part of fermented base was diluted with 3 parts of a pasteurized sugar syrup (16% sucrose), homogenized and cooled down to 5° C. For the sedimentation experiment, a specified amount of the fresh product was filled in turbiscan glass tubes and stored at 5° C. for 29 days until measurement in the Turbiscan. It surprisingly turned out that a significant lower degree of sedimentation was seen in a fermented milk product made from CHCC19845, compared to the mother strain LC-01. This reduces the need for addition of stabilizer and/or thickeners (such as polysaccharides, starch, pectin, etc.) to fermented milk products.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Example 5: Manufacture of Milk Products Containing Phage Resistant Mutant—Assessment of Cell Count During Shelf Life Fermented diluted milk drinks were produced with the strains CHCC19845 and its corresponding wild-type each inoculated at a 0.0025% (=0.25×10^6 cfu/g milk), 0.005% (=0.5×10^6 cfu/g milk) and 0.01% (=1×10^6 cfu/g milk) rate. Reconstituted skimmed milk (14%) with addition of 4% glucose (90° C., 60 minutes) was inoculated with CHCC19845 or its corresponding wild-type as single acidifier and fermented for approximately 72 hours. Thereafter, one part of fermented base was diluted with 3 parts of a pasteurized sugar syrup (16% sucrose), homogenized and cooled to 5° C. The products were stored for 40 days at 5° C.

Cell counts were determined on MRS-agar pH 6.5 Difco with the pour plate method at day 1, day 21 and day 40. The plates were anaerobically incubated at 37° C. for 3 days.

Thereafter, colony forming units were counted.

Figure 3:
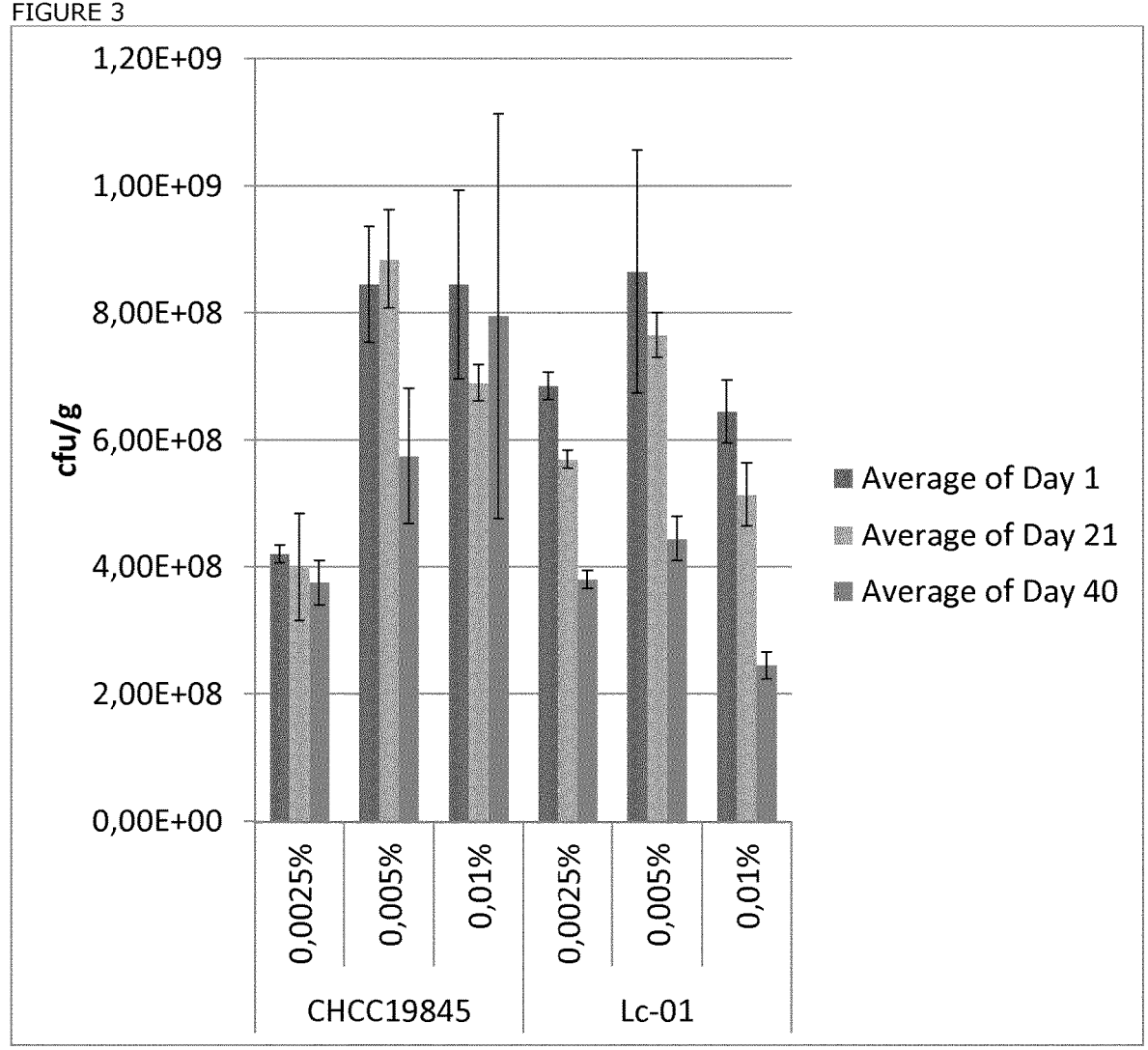

It was observed that the cell count during shelf life in fermented milk products made from CHCC19845 was stable along 40 days, compared to products made from the wild type. As illustrated in FIG. 3, the Lc-01 from which CHCC19845 is derived show a clear tendency of declining cell-counts over time, whereas the CHCC19845 mutants show a more constant cell count per gram over time.

DRAWINGS

FIG. 1: Turbiscan measurements of the height clarification zone in mm. The height of the clarification zone gives an indication of the degree of sedimentation. The smaller the clarification zone, the less sedimentation is seen.

Figure 2:
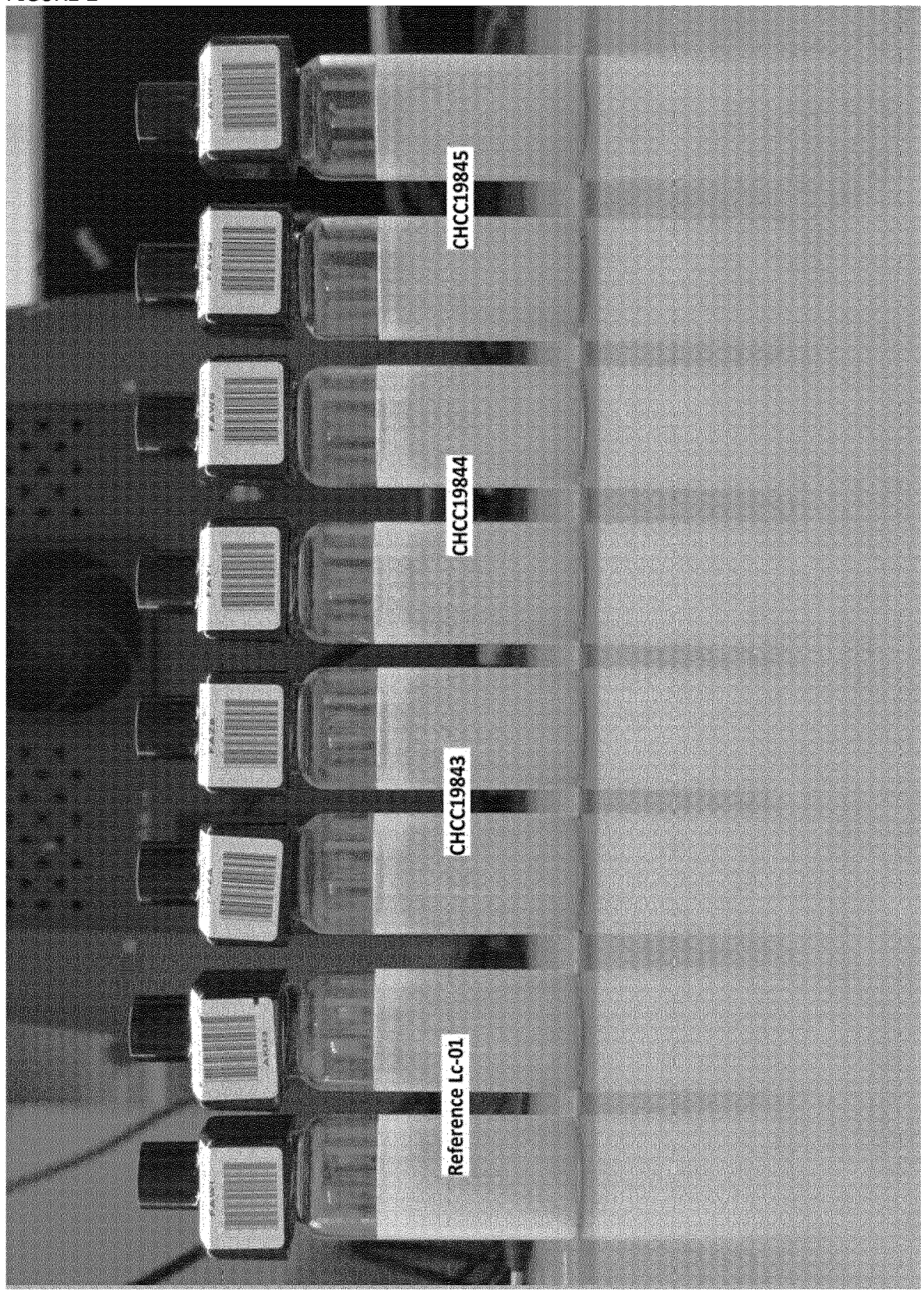

FIG. 2: Duplicate samples in turbiscan tubes. Already in the tubes, it can be seen that the product produced with the reference LC-01 (CHCC2115) has a larger clarification zone than the product produced with CHCC19845. This indicates that there is a lower degree of sedimentation in the product with CHCC19845.

FIG. 3: Cell count during shelf life in fermented milk products made from CHCC19845 was stable along 40 days, compared to products made from the wild type. Lc-01 (the bars on the right) from which CHCC19845 is derived show a clear tendency of declining cell-counts over time, whereas the CHCC19845 mutants show a more higher cell count stability per gram over time DEPOSITS and EXPERT SOLUTION The *Lactobacillus paracasei* ssp. *paracasei* CHCC19845 strain was deposited at Leibniz Institute DSMZ—German Collection of Microorganisms and Cell Cultures (Deutsche Sammlung von Mikroorganismen and Zellkulturen), Inhoffenstr. 7B, D-38124 Braunschweig the 17 Mar. 2016 and given the accession number DSM32276.

The bacteriophage CHPC1256 was also deposited at DSMZ the 17 Mar. 2016 and given the accession number DSM32286.

The mother strain LC-01 (CHCC2115) was deposited at DSMZ the 27 Jun. 2007 and given the accession number DSM19465.

The deposits were made according to the Budapest treaty on the international recognition of the deposit of microorganisms for the purposes of patent procedure.

The Applicant requests that a sample of the deposited microorganism should be made available only to an expert approved by the Applicant.

SEQUENCE LISTING

```
SEQ ID NO. 1: LOCUS CHCC2115_eps7M 1461 bp DNA
    1 ATGCAAGTTT TGGAGATTTT TATGAAAGTA ATCAAGAACT TTTTTTGGAA TGCGGGTTAT

61 CAGGTCTTCG TCCTGATTGT GCCGCTGGTA ACTGTACCTT ATATTAATCG AGTACTAGGA

121 CCGACAGGCG TTGGGATAAA TGCGTTCACT AACTCAATTG TCCAATACTT TATTCTCTTT

181 GGTAGTCTGG GTATTAACCT TTATGGGAAT CGGGGCACAG CTTATCGAAG AGATGATCGA

241 AAAGCGCTGA CCACCTATTT TTGGGAAGTC ACCATACTTC GATTTGTGAC GATTGGTATA

301 GCTGTGCTTG CGTATCTCAT GTTTATATTT GCCGTCGATG AGTATCGTGT TTTTTATCTT

361 GCTCAAGGCG TTATGCTTTT GGGAACAGCG TTTGATATTT CGTGGTTTTT CCAAGGATTA

421 GAAAACTTTC GGGTAACGGT GGTTCGTAAT GTGTTGGTGC GGATCGCTTC CCTCATTCTG

481 ATTTTCCTGT TAGTGCATAA AGCAGATGAT ACTGCTTTGT ATATTCTGAT CATGTCTGGC

541 TCACAGATGT TGGGGAATCT AACATTCTGG CCCTCATTAC GCGCAAATCT GACACATTTT

601 CCGAAACTGT CAAGCCTGAA CATCTGGCAG CATATTAAAC CGGCGTTCCT TCTATTGATT

661 CCGCAACTGG CGATTCAAAT TTATGTTCAA CTGAATAAAA CGATGCTTGG AATTTTACAG

721 GGTGTTACGG CATCTGGTTT TTACGAAAGT TCGGACAAAA TCATTAAAAT GTTATTGGCT

781 CTTGTGACAG CAACCGGCAC CGTCTTATTG CCGCATGTGG CCCATTATTT TGCCCAAGGT

841 GATCACGATG CCGTCAAACG CTCATTAGAA ACATCGATGC ACGTGATTTT GGTTATTGCT

901 TTTCCTTTAG CCTTTGGGAT TGCGGCGGTT TCCACAACGT TTACTTATTA TTTTTTTAGC
```

```
-continued
 961 ACAAAGTTTA TGCCCGTGGC ACCCTTGATG GCAGCTGAAG CGATTGTCGT CATTCCGATT

1021 TCGATTGCGA GTGCCATTGG TGTGCAATAT TTGCTGCCAA CTAACCAAGT TAAGTCATAT

1081 ACTGTCTCAG TTATTTTGGG ATCCATCGTT AATATTGTAG TGAATGTGCC TCTTATTCTG

1141 TGGTTAGGAA CAATGGGCGC TGTGATTGGC ACTATCCTTT CTGAATCAGT CGTGACGATT

1201 TATCAGGTCT ATGCTATTAA AAATCAGCTT GATCTCAGAG GCTTGTTTAG TGAATCATGG

1261 AAGTATTGCC TCAGCGCGGT CGTGATGTTT GGTGTTGTAA AAGGTCTTGA GATTGCCTGG

1321 TCCACCAGCT TGATCGGCCT AGTTGTTGAA GTTTTGATTG GTATGGTGGT GTACTTTGTG

1381 GTGCTGTTGG GGTTACGACC GCACATTATC ATTGGGTATG TTCGCCCATA TGTCGATCAG

1441 ATGCGTCGGC GTCTTCGTTA A

SEQ ID NO. 2: LOCUS CHCC2115_eps7M_p 487 aa
   1 MQVLEIFMKV IKNFFWNAGY QVFVLIVPLV TVPYINRVLG PTGVGINAFT NSIVQYFILF

61 GSLGINLYGN RGTAYRRDDR KALTTYFWEV TILRFVTIGI AVLAYLMFIF AVDEYRVFYL

121 AQGVMLLGTA FDISWFFQGL ENFRVTVVRN VLVRIASLIL IFLLVHKADD TALYILIMSG

181 SQMLGNLTFW PSLRANLTHF PKLSSLNIWQ HIKPAFLLLI PQLAIQIYVQ LNKTMLGILQ

241 GVTASGFYES SDKIIKMLLA LVTATGTVLL PHVAHYFAQG DHDAVKRSLE TSMHVILVIA

301 FPLAFGIAAV STTFTYYFFS TKFMPVAPLM AAEAIVVIPI SIASAIGVQY LLPTNQVKSY

361 TVSVILGSIV NIVVNVPLIL WLGTMGAVIG TILSESVVTI YQVYAIKNQL DLRGLFSESW

421 KYCLSAVVMF GVVKGLEIAW STSLIGLVVE VLIGMVVYFV VLLGLRPHII IGYVRPYVDQ

481 MRRRLR*

SEQ ID NO. 3: LOCUS CHCC2115_glycosyltransferase 885 bp DNA
   1 ATGGTCAAAG TTTCAATCAT TATTCCTGCT TACAATGCTC CTACCACTCT AAAGCGCGCT

61 GTTCAGTCTG TCCGTAAACA AACCTTGAAC GATTTTGAAA TATTAATCGT CAATAATGGA

121 TCGACGGATC AGACAGCAGC AGTTATGTCA CACCTTGTCC AAGCTGACCC TCGGATACAC

181 ATTCTGCAAA GTATGAAAGG CGCGCAGCCG CGCTCGTAATC AAGGACTGAC AAAGGCTCAA

241 GGTACTTTTA TCCAGTTTCT GGACGCGGAT GACGAACTTG CTGTCAATAA GCTGGAAGTG

301 GGCAGCAGTT ATTTGACGAA TCATCCAAAC AGTAGCGCAT ACATCACGGC GGCTAAATAT

361 CAAAATGATA AGCGTGGCGA TGAGAGCATT CGCCAGATTC CGCTAACATC CGCAGCACCT

421 TTATTAAAGG CAAATTATTT GCCAATGAGT GCACCGCTTG TGAGGAAAAG TGCGCTCATA

481 AAGCCCTTTA GAGAAGATCT TGAATATAAT GAGGACTGGT TATTTTGGGC TGAAAACCTG

541 TACAAAAAAG AGATAGCTGT TAGCTCGACA GTTGGCACAA CGATCCATAT TACGTCTGCT

601 AATACTATGA CTCAGTTTGA TCGAATGCAA ATGTACGAGT GTTATGTGCG GGAATTTTA

661 AAAGAAGAAT TTTCGGCACG CGGTCCTCGC TACTGGGCGC GGGATATGCG CTATGCACTC

721 AATTATCTAC TTAGCGCGTC GGATGCAACG AGCGAGGACC TGAAGCTATC TAAGACAATG

781 GCTTGGCCAA TCCGGTTTAG CCGTCTATTA TTAGCTGTGC CACCGTTGCG AGCGGTTATT

841 ACAAAAAAAC GTAATGCCGT GAAAGCGCGT AGTCAATATG GATAA

SEQ ID NO. 4: LOCUS CHCC2115_glycosyltransferase_p 295 aa
   1 MVKVSIIIPA YNAATTLKRA VQSVRKQTLN DFEILIVNNG STDQTAAVMS HLVQADPRIH

61 ILQSMKGRSR ARNQGLTKAQ GTFIQFLDAD DELAVNKLEV GSSYLTNHPN SSAYITAAKY

121 QNDKRGDESI RQIPLTSAAP LLKANYLPMS APLVRKSALI KPFREDLEYN EDWLFWAENL

181 YKKEIAVSST VGTTIHITSA NTMTQFDRMQ MYECYVRGIL KEEFSARGPR YWARDMRYAL

241 NYLLSASDAT SEDLKLSKTM AWPIRFSRLL LAVPPLRAVI TKKRNAVKAR SQYG*
```

REFERENCES

All references cited in this patent document are hereby incorporated herein in their entirety by reference.

The invention claimed is:

1. A mutant strain of the species *Lactobacillus paracasei* or *Lactobacillus casei*, wherein the mutant strain is resistant against infection with the phage CHPC1256 deposited at Deutsche Sammlung von Mikroorganismen and Zellkulturen (DSMZ) under Accession Number DSM32286.

2. The mutant strain of claim 1, wherein the mutant strain maintains a viability of at least 75% in a fermented milk matrix when stored at 5° C. for 40 days.

3. The mutant strain of claim 2, wherein viability of the strain is assessed by inoculating the strain in the fermented milk matrix in an amount of $10^9$ colony forming units (CFU) per kg milk, optionally as a single acidifier.

4. The mutant strain of claim 1, wherein the strain has one or more mutations selected from (a) a mutation in the gene eps7M that results in a change in structure of the encoded protein and (b) a mutation in the gene LCABL_02330 encoding a glycosyltransferase that results in partial or full inactivation of the glycosyltransferase compared to parent *Lactobacillus paracasei* or *Lactobacillus casei*.

5. The mutant strain of claim 1, wherein the strain has a mutation in the gene LCABL_02330 that is a truncation.

6. A mutant strain resistant against infection with the phage CHPC1256 obtained by a process comprising:
   subjecting the *Lactobacillus paracasei* strain LC-01 deposited at DSMZ under Accession No. DSM19465 to mutagenesis to obtain mutant strains;
   exposing the mutant strains to the phage CHPC1256 deposited at DSMZ under Accession No. DSM32286; and
   selecting a mutant strain that is resistant against the phage CHPC1256.

7. A mutant strain of *Lactobacillus paracasei*, wherein the mutant strain is strain CHCC19845, deposited at DSMZ under Accession No. DSM 32276.

8. A mutant strain of the species *Lactobacillus paracasei* or *Lactobacillus casei*, wherein the mutant strain has a mutation in the gene eps7M that results in a change in structure of the encoded protein.

9. A method for obtaining a mutant strain of a mother strain of the species *Lactobacillus paracasei* or *Lactobacillus casei* according to claim 1, comprising:
   (i) subjecting a culture of the mother strain to mutagenesis to obtain mutant strains;
   (ii) exposing the mutant strains to a phage that attacks the mother strain, wherein the phage is phage CHPC1256 deposited at DSMZ under Accession No. DSM32286; and
   (iiia) selecting a mutant strain that is resistant to the phage, or
   (iiib) selecting a mutant strain that is cell count-stabilized.

10. A method according to claim 9, wherein the mother strain is selected from CHCC2115 (DSM19465), LC-01 (DSM19465), *L. casei* DG (CNCM I-1572), LPC-37 (ATCC SD5275), CHCC14676 (DSM25612), *L. casei* 431 (CRL431), ATCC 55544, *Lactobacillus paracasei* F19, LMG-17806, *Lactobacillus paracasei* subsp. *paracasei* LP-33, CCTCC M204012, and CNCM I-1518, or mutants or variants of any of these.

11. A method for obtaining a phage resistant and/or cell count-stabilized mutant strain of the species *Lactobacillus paracasei* or *Lactobacillus casei* according to claim 1, comprising one or more of:
   genetically engineering a mutation in the gene eps7M that results in a change in the encoded protein or in the capsular polysaccharide structure, and
   genetically engineering a mutation in the gene LCABL_02330 encoding a glycosyltransferase that results a change in the capsular polysaccharide structure.

12. A method of fermenting a milk substrate, comprising adding a strain of claim 1 to the milk substrate.

13. A bacterial culture containing at least $10^8$ CFU/per gram of a strain of claim 1.

14. A bacterial culture of claim 13, in frozen or dried form.

15. A fermented milk food product containing a strain of claim 1.

16. A fermented milk food product of claim 15, wherein the product is a drinkable yogurt.

17. A mutant strain of the species *Lactobacillus paracasei* or *Lactobacillus casei*, wherein the mutant strain has one or more mutations selected from (a) a mutation in the gene eps7M that results in a change in structure of the encoded protein, and (b) a mutation in the gene LCABL_02330 encoding a glycosyltransferase that results in partial or full inactivation of the glycosyltransferase compared to parent *Lactobacillus paracasei* or *Lactobacillus casei*.

18. The mutant strain of claim 17, wherein the strain has a mutation in the gene LCABL_02330 that is a truncation.

\* \* \* \* \*

```
                        SEQUENCE LISTING

<160> NUMBER OF SEQ ID NOS: 4

<210> SEQ ID NO 1
<211> LENGTH: 1461
<212> TYPE: DNA
<213> ORGANISM: Lactobacillus

<400> SEQUENCE: 1
atgcaagttt tggagatttt tatgaaagta atcaagaact ttttttggaa tgcgggttat      60
caggtcttcg tcctgattgt gccgctggta actgtacctt atattaatcg agtactagga     120
ccgacaggcg ttgggataaa tgcgttcact aactcaattg tccaatactt tattctcttt     180
ggtagtctgg gtattaacct ttatgggaat cggggcacag cttatcgaag agatgatcga     240
aaagcgctga ccacctattt tgggaagtc accatacttc gatttgtgac gattggtata      300
gctgtgcttg cgtatctcat gtttatattt gccgtcgatg agtatcgtgt tttttatctt     360
gctcaaggcg ttatgctttt gggaacagcg tttgatattt cgtggttttt ccaaggatta     420
gaaaactttc gggtaacggt ggttcgtaat gtgttggtgc ggatcgcttc cctcattctg     480
attttcctgt tagtgcataa agcagatgat actgctttgt atattctgat catgtctggc     540
tcacagatgt tggggaatct aacattctgg ccctcattac gcgcaaatct gacacatttt     600
ccgaaactgt caagcctgaa catctggcag catattaaac cggcgttcct tctattgatt     660
ccgcaactgg cgattcaaat ttatgttcaa ctgaataaaa cgatgcttgg aattttacag     720
ggtgttacgg catctggttt ttacgaaagt tcggacaaaa tcattaaaat gttattggct     780
cttgtgacag caaccggcac cgtcttattg ccgcatgtgg cccattattt tgcccaaggt     840
gatcacgatg ccgtcaaacg ctcattagaa acatcgatgc acgtgatttt ggttattgct     900
tttcctttag cctttgggat tgcggcggtt tccacaacgt ttacttatta tttttttagc     960
acaaagttta tgcccgtggc acccttgatg gcagctgaag cgattgtcgt cattccgatt    1020
tcgattgcga gtgccattgg tgtgcaatat ttgctgccaa ctaaccaagt taagtcatat    1080
actgtctcag ttattttggg atccatcgtt aatattgtag tgaatgtgcc tcttattctg    1140
tggttaggaa caatgggcgc tgtgattggc actatccttt ctgaatcagt cgtgacgatt    1200
tatcaggtct atgctattaa aaatcagctt gatctcagag gcttgtttag tgaatcatgg    1260
aagtattgcc tcagcgcggt cgtgatgttt ggtgttgtaa aaggtcttga gattgcctgg    1320
tccaccagct tgatcggcct agttgttgaa gttttgattg gtatggtggt gtactttgtg    1380
gtgctgttgg ggttacgacc gcacattatc attgggtatg ttcgcccata tgtcgatcag    1440
atgcgtcggc gtcttcgtta a                                              1461

<210> SEQ ID NO 2
<211> LENGTH: 486
<212> TYPE: PRT
<213> ORGANISM: Lactobacillus

<400> SEQUENCE: 2

Met Gln Val Leu Glu Ile Phe Met Lys Val Ile Lys Asn Phe Phe Trp
1               5                   10                  15

Asn Ala Gly Tyr Gln Val Phe Val Leu Ile Val Pro Leu Val Thr Val
            20                  25                  30
```

```
Pro Tyr Ile Asn Arg Val Leu Gly Pro Thr Gly Val Gly Ile Asn Ala
            35                  40                  45

Phe Thr Asn Ser Ile Val Gln Tyr Phe Ile Leu Phe Gly Ser Leu Gly
 50                  55                  60

Ile Asn Leu Tyr Gly Asn Arg Gly Thr Ala Tyr Arg Arg Asp Asp Arg
 65                  70                  75                  80

Lys Ala Leu Thr Thr Tyr Phe Trp Glu Val Thr Ile Leu Arg Phe Val
                85                  90                  95

Thr Ile Gly Ile Ala Val Leu Ala Tyr Leu Met Phe Ile Phe Ala Val
               100                 105                 110

Asp Glu Tyr Arg Val Phe Tyr Leu Ala Gln Gly Val Met Leu Leu Gly
               115                 120                 125

Thr Ala Phe Asp Ile Ser Trp Phe Phe Gln Gly Leu Glu Asn Phe Arg
               130                 135                 140

Val Thr Val Val Arg Asn Val Leu Val Arg Ile Ala Ser Leu Ile Leu
145                 150                 155                 160

Ile Phe Leu Leu Val His Lys Ala Asp Asp Thr Ala Leu Tyr Ile Leu
               165                 170                 175

Ile Met Ser Gly Ser Gln Met Leu Gly Asn Leu Thr Phe Trp Pro Ser
               180                 185                 190

Leu Arg Ala Asn Leu Thr His Phe Pro Lys Leu Ser Ser Leu Asn Ile
               195                 200                 205

Trp Gln His Ile Lys Pro Ala Phe Leu Leu Ile Pro Gln Leu Ala
               210                 215                 220

Ile Gln Ile Tyr Val Gln Leu Asn Lys Thr Met Leu Gly Ile Leu Gln
225                 230                 235                 240

Gly Val Thr Ala Ser Gly Phe Tyr Glu Ser Ser Asp Lys Ile Ile Lys
               245                 250                 255

Met Leu Leu Ala Leu Val Thr Ala Thr Gly Thr Val Leu Leu Pro His
               260                 265                 270

Val Ala His Tyr Phe Ala Gln Gly Asp His Asp Ala Val Lys Arg Ser
               275                 280                 285

Leu Glu Thr Ser Met His Val Ile Leu Val Ile Ala Phe Pro Leu Ala
               290                 295                 300

Phe Gly Ile Ala Ala Val Ser Thr Thr Phe Thr Tyr Phe Phe Ser
305                 310                 315                 320

Thr Lys Phe Met Pro Val Ala Pro Leu Met Ala Ala Glu Ala Ile Val
               325                 330                 335

Val Ile Pro Ile Ser Ile Ala Ser Ala Ile Gly Val Gln Tyr Leu Leu
               340                 345                 350

Pro Thr Asn Gln Val Lys Ser Tyr Thr Val Ser Val Ile Leu Gly Ser
               355                 360                 365

Ile Val Asn Ile Val Val Asn Val Pro Leu Ile Leu Trp Leu Gly Thr
               370                 375                 380

Met Gly Ala Val Ile Gly Thr Ile Leu Ser Glu Ser Val Val Thr Ile
385                 390                 395                 400

Tyr Gln Val Tyr Ala Ile Lys Asn Gln Leu Asp Leu Arg Gly Leu Phe
               405                 410                 415

Ser Glu Ser Trp Lys Tyr Cys Leu Ser Ala Val Val Met Phe Gly Val
               420                 425                 430

Val Lys Gly Leu Glu Ile Ala Trp Ser Thr Ser Leu Ile Gly Leu Val
               435                 440                 445
```

Val Glu Val Leu Ile Gly Met Val Val Tyr Phe Val Val Leu Leu Gly
450                 455                 460

Leu Arg Pro His Ile Ile Ile Gly Tyr Val Arg Pro Tyr Val Asp Gln
465                 470                 475                 480

Met Arg Arg Arg Leu Arg
                485

<210> SEQ ID NO 3
<211> LENGTH: 885
<212> TYPE: DNA
<213> ORGANISM: Lactobacillus

<400> SEQUENCE: 3

```
atggtcaaag tttcaatcat tattcctgct tacaatgctg ctaccactct aaagcgcgct     60
gttcagtctg tccgtaaaca aaccttgaac gattttgaaa tattaatcgt caataatgga    120
tcgacggatc agacagcagc agttatgtca cccttgtcc aagctgaccc tcggatacac    180
attctgcaaa gtatgaaagg cgcagccgc gctcgtaatc aaggactgac aaaggctcaa    240
ggtactttta tccagtttct ggacgcggat gacgaacttg ctgtcaataa gctggaagtg    300
ggcagcagtt atttgacgaa tcatccaaac agtagcgcat acatcacggc ggctaaaatat   360
caaaatgata gcgtggcga tgagagcatt cgccagattc cgctaacatc cgcagcacct    420
ttattaaagg caaattattt gccaatgagt gcaccgcttg tgaggaaaag tgcgctcata    480
aagcccttta gaagatct tgaatataat gaggactggt tattttgggc tgaaaacctg    540
tacaaaaaag atagctgt tagctcgaca gttggcacaa cgatccatat tacgtctgct    600
aatactatga ctcagtttga tcgaatgcaa atgtacgagt gttatgtgcg gggattttta    660
aaagaagaat tttcggcacg cggtcctcgc tactgggcgc gggatatgcg ctatgcactc    720
aattatctac ttagcgcgtc ggatgcaacg agcgaggacc tgaagctatc taagacaatg    780
gcttggccaa tccggtttag ccgtctatta ttagctgtgc caccgttgcg agcggttatt    840
acaaaaaaac gtaatgccgt gaaagcgcgt agtcaatatg gataa                   885
```

<210> SEQ ID NO 4
<211> LENGTH: 294
<212> TYPE: PRT
<213> ORGANISM: Lactobacillus

<400> SEQUENCE: 4

Met Val Lys Val Ser Ile Ile Ile Pro Ala Tyr Asn Ala Ala Thr Thr
1               5                   10                  15

Leu Lys Arg Ala Val Gln Ser Val Arg Lys Gln Thr Leu Asn Asp Phe
            20                  25                  30

Glu Ile Leu Ile Val Asn Asn Gly Ser Thr Asp Gln Thr Ala Ala Val
        35                  40                  45

Met Ser His Leu Val Gln Ala Asp Pro Arg Ile His Ile Leu Gln Ser
    50                  55                  60

Met Lys Gly Arg Ser Arg Ala Arg Asn Gln Gly Leu Thr Lys Ala Gln
65                  70                  75                  80

Gly Thr Phe Ile Gln Phe Leu Asp Ala Asp Asp Glu Leu Ala Val Asn
                85                  90                  95

Lys Leu Glu Val Gly Ser Ser Tyr Leu Thr Asn His Pro Asn Ser Ser
            100                 105                 110

Ala Tyr Ile Thr Ala Ala Lys Tyr Gln Asn Asp Lys Arg Gly Asp Glu
        115                 120                 125

```
Ser Ile Arg Gln Ile Pro Leu Thr Ser Ala Ala Pro Leu Leu Lys Ala
    130             135             140

Asn Tyr Leu Pro Met Ser Ala Pro Leu Val Arg Lys Ser Ala Leu Ile
145             150             155             160

Lys Pro Phe Arg Glu Asp Leu Glu Tyr Asn Glu Asp Trp Leu Phe Trp
            165             170             175

Ala Glu Asn Leu Tyr Lys Lys Glu Ile Ala Val Ser Ser Thr Val Gly
            180             185             190

Thr Thr Ile His Ile Thr Ser Ala Asn Thr Met Thr Gln Phe Asp Arg
        195             200             205

Met Gln Met Tyr Glu Cys Tyr Val Arg Gly Ile Leu Lys Glu Glu Phe
    210             215             220

Ser Ala Arg Gly Pro Arg Tyr Trp Ala Arg Asp Met Arg Tyr Ala Leu
225             230             235             240

Asn Tyr Leu Leu Ser Ala Ser Asp Ala Thr Ser Glu Asp Leu Lys Leu
            245             250             255

Ser Lys Thr Met Ala Trp Pro Ile Arg Phe Ser Arg Leu Leu Leu Ala
            260             265             270

Val Pro Pro Leu Arg Ala Val Ile Thr Lys Lys Arg Asn Ala Val Lys
        275             280             285

Ala Arg Ser Gln Tyr Gly
    290
```